United States Patent [19]

Ring

[11] Patent Number: 4,548,602
[45] Date of Patent: Oct. 22, 1985

[54] INTERCOSTAL TUBE

[76] Inventor: Edward M. Ring, 621 S. New Ballas Rd., St. Louis, Mo. 63141

[21] Appl. No.: 517,724

[22] Filed: Jul. 27, 1983

[51] Int. Cl.⁴ ........................................ A61M 25/00
[52] U.S. Cl. .................................................. 604/280
[58] Field of Search ................ 604/280, 170, 272, 239

[56] References Cited

U.S. PATENT DOCUMENTS 2,458,305  1/1949  Sanders ........................... 604/170 X
3,067,742 12/1962  Linke et al. ..................... 604/239 X
3,190,290  6/1965  Alley et al. ........................... 604/280

Primary Examiner—Stephen C. Pellegrino
Attorney, Agent, or Firm—Rogers, Howell, Renner, Moore & Haferkamp

[57] ABSTRACT

An intercostal tube designed to be inserted between the ribs of a patient for drainage purposes of the chest area, made of relatively stiff but pliable plastic material with its inserting end at a sharp taper with a blunted end, that by being arcuate, preserves the adequate rigidity to permit the tube to be compressed transversely and inserted between the ribs, without widening the portion of the tube required to pass between the ribs, which would require a larger opening in the patient, and increased pain, and that avoids snagging tissue during insertion.

2 Claims, 4 Drawing Figures

INTERCOSTAL TUBE

BACKGROUND OF THE INVENTION

Intercostal tubes have been heretofore made with squared ends. When such a tube is inserted between the ribs, it is very difficult to insert because of the squared end and the large area that must be inserted. Accordingly, the end to be inserted is usually squeezed or compressed transversely to make the tube narrower to require less of an incision in order to pass between the ribs. But this squeezing increases the vertical dimension of the tube and thereby requires a larger opening in the area between the ribs, which can cause the patient pain. It is also recognized that some tubes for other uses have been made with sloping ends but not of the present material and not with the present type of end that can be inserted between the ribs. An example of this is the Sanders U.S. Pat. No. 2,458,305. Also intravascular catheters have been made with trocars wherein the trocar has a sloping end. But in that case, the trocar is usually of metal and it is of a very small size designed to enter a vein or the like part of the human body. Thus it does not have the problem of being flexible and yet being stiff enough to be inserted between the ribs, or of being widened upon being squeezed.

Figure 1:
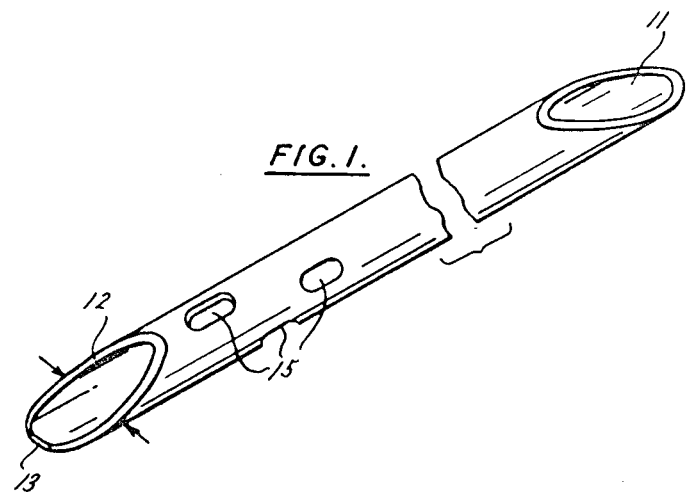
FIG. 1 is a view of an intercostal tube broken away, showing the present invention.
Figure 2:
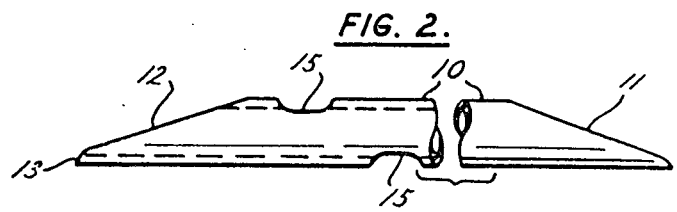
FIG. 2 is a top plan view thereof.

DESCRIPTION OF PREFERRED EMBODIMENT:

The tube 10 is here shown as having its outer, discharge end 11. Its inner other end is given an acute sloping edge 12 that has an angle of approximately twenty-five degrees to the axis of the tube. Preferably the sloping edge does not extend entirely across the tube but it stops, leaving an end edge 13 that is arcuate and thereby stronger against bending under axial pressure than the end of the tube would be if the sloping edge 12 went entirely across the tube, and the end were nearly pointed.

The tube has drainage openings 15 spaced from its end 12, to admit fluids from the body after insertion. These fluids can drain out the outer end 11.

The tube may be made of one of the polyhaloginated polyethylenes or its equivalent plastic material suitable for medical use. Typically, these products are known as Tygon or Teflon. They are flexible but rather resistant to distortion transversely of the tube. The tubes are normally about 18 to 20 inches long, to 40 French diameter, with walls approximately 2 millimeters thick for a tube of approximately 14 millimeters outside diameter, or 40 French.

Figure 4:
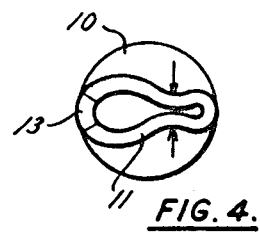
FIG. 4 is an end view of the present invention showing the sloping end of the tube squeezed for insertion.
Figure 3:
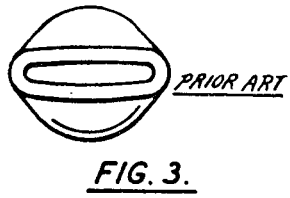
FIG. 3 is an end view of a squared-end tube of the prior art with the end of the tube compressed to narrow it for its entrance between the ribs.

In use:

The tube of the present invention can be inserted between the ribs into the thoracic area. In this, the lip 13 remains strong enough that the end of the tube will not collapse and bend over, this result coming from the fact that the lip is somewhat blunt and is arcuate in shape. The blunt end therefore does not snag the tissues when the tube is being inserted. The steep slope 12 permits the tube to be inserted between the ribs with the minimum size of the opening between the ribs to receive the tube. Usually a clamp is applied to the inserted end of the tube, as is indicated by the arrows in FIGS. 1 and 4. This squeezes the end, as shown in FIG. 4. Because of the sloping edges, and the cut-away sides, the squeezing applied along the sloping end does not bulge lateral parts of the tube significantly beyond the diameter of the tube. In FIG. 3, the latter extension of a square-ended tube, when squeezed, is illustrated. Such extension causes pain to the patient.

Thus the invention does not require a trocar as is true of the Calinog U.S. Pat. No. 3,703,899. It remains flexible so that its axis can be bent. It is insertable without the trocar because it remains rigid enough with the extreme slope of the edge 12 and with the enlarged end produced by the cutoff 13.

There are various changes and modifications which may be made to applicant's invention as would be apparent to those skilled in the art. However, any of these changes or modifications are included in the teaching of applicant's disclosure and he intends that his invention be limited only by the scope of the claims as appended hereto.

What is claimed is:

1. An intercostal tube of plastic material, the tube being of a size to enable drainage from a body cavity into which it is inserted, and being flexible about its longitudinal axis but relatively resistant to transverse crushing force; the tube having a sloping tip end portion for insertion into the body by way of a passage therein made such as one between the ribs; the end of the tube being blunted to reduce its tendency to bend or to snag body tissue during insertion, the sloping tip, when viewed transversely of the tube axis, extending in a single slope from a point on the surface of the tube toward the end of the tube and toward the opposite side of the tube but terminating short of the opposite side of the tube, leaving a continuous end that is blunted and that extends around the tube, and the blunted part of which when viewed from the end of the tube, is arcuate and is relatively rigid against collapse upon being forced through a passage such as the one between the ribs.

2. The tube of claim 1, the slope being about twenty-five degrees to the longitudinal axis, and the tip of the tube being rigid enough to be inserted between the ribs without bending.

* * * * *